(12) United States Patent
Servidio

(10) Patent No.: US 7,081,137 B1
(45) Date of Patent: Jul. 25, 2006

(54) KNEE PROSTHESIS WITH EXTENDED RANGE OF MOTION

(75) Inventor: Damon J. Servidio, Montville, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 396 days.

(21) Appl. No.: 10/601,349

(22) Filed: Jun. 23, 2003

(51) Int. Cl.
*A61F 2/38* (2006.01)

(52) U.S. Cl. ................................... 623/20.14

(58) Field of Classification Search ............. 623/20.31, 623/20.14, 20.27, 20.24, 20.32
See application file for complete search history.

(56) References Cited

U.S. PATENT DOCUMENTS

| | | | |
|---|---|---|---|
| 3,748,662 A | 7/1973 | Helfet | |
| 4,261,064 A | 4/1981 | Helfet | |
| 4,309,778 A * | 1/1982 | Buechel et al. | 623/20.29 |
| 4,888,021 A | 12/1989 | Forte et al. | |
| 4,944,756 A | 7/1990 | Kenna | |
| 5,011,496 A | 4/1991 | Forte et al. | |
| 5,059,216 A | 10/1991 | Winters | |
| 5,071,438 A | 12/1991 | Jones et al. | |
| 5,133,758 A * | 7/1992 | Hollister | 623/20.31 |
| 5,147,405 A | 9/1992 | Van Zile et al. | |
| 5,192,328 A | 3/1993 | Winters | |
| 5,219,362 A | 6/1993 | Tuke et al. | |
| 5,236,461 A | 8/1993 | Forte | |
| 5,282,870 A * | 2/1994 | Moser et al. | 623/20.31 |
| 5,395,401 A | 3/1995 | Bahler | |
| 5,871,546 A | 2/1999 | Colleran et al. | |
| 5,879,394 A | 3/1999 | Ashby et al. | |
| 5,935,173 A | 8/1999 | Roger et al. | |
| 5,964,808 A | 10/1999 | Blaha et al. | |
| 6,013,103 A | 1/2000 | Kaufman et al. | |
| 6,039,764 A * | 3/2000 | Pottenger et al. | 623/20.32 |
| 6,203,576 B1 | 3/2001 | Afriat et al. | |
| 6,325,828 B1 | 12/2001 | Dennis et al. | |
| 6,406,497 B1 * | 6/2002 | Takei | 623/20.31 |
| 6,494,915 B1 | 12/2002 | Villar Gonzalez et al. | |

OTHER PUBLICATIONS

Iwaki, H. et al, Tibiofemoral movement 1: the shapes and relative movements of the femur and tibia in the . . . J Bone Joint Surg (Br), 2000:82-B, 1189-95.

(Continued)

*Primary Examiner*—Pedro Philogene
(74) *Attorney, Agent, or Firm*—Arthur Jacob

(57) ABSTRACT

In a knee prosthesis, the condylar surfaces of a femoral component engage corresponding articular surfaces of a tibial component along prescribed tracks of predetermined curvature which enable relative rotation between the femoral component and the tibial component about a longitudinal axis during articulation of the knee prosthesis, and at least the condylar surfaces or the articular surfaces are flared in a direction away from corresponding articular surfaces or condylar surfaces along engaged posterior and anterior portions of the condylar surfaces and articular surfaces to provide an increased area of contact in deep flexion and in extended hyperextension for reducing contact stresses and concomitant wear while militating against unwanted distraction of the knee prosthesis. In addition, the radius of curvature of the condylar surfaces is reduced along posterior portions of the condylar surfaces to further avoid distraction of the knee prosthesis in deep flexion, thereby enabling deep flexion with greater ease and without excessive contact forces between the femoral component and the tibial component in deep flexion.

44 Claims, 14 Drawing Sheets

OTHER PUBLICATIONS

Hill, P.F. et al, Tibiofemoral movement 2: the loaded and unloaded living knee studied by MRI, J Bone Joint Surg (Br), 2000:82-B, 1196-8.

Nakagawa, S. et al, Tibiofemoral movement 3: full flexion in the living knee studied by MRI, J Bone Surg (Br), 2000:82-B, 1199-2000.

Karrholm, J. et al, Tibiofemoral movement 4: changes of axial tibial rotation caused by forced rotation . . . , J Bone Joint Surg (Br), 2000:82-B, 1201-3.

Howmedica Inc., Duracon, the femoral system, 1994, p. 5.

Howmedica Inc., Duracon, the tibial system, 1994, p. 7.

* cited by examiner

0° FLEXION

45° FLEXION

60° FLEXION

90° FLEXION

110° FLEXION

150° FLEXION

0° FLEXION

4° HYPEREXTENSION

8° HYPEREXTENSION

12° HYPEREXTENSION

KNEE PROSTHESIS WITH EXTENDED RANGE OF MOTION

BACKGROUND OF THE INVENTION

1. Field of the Invention

The present invention relates generally to the replacement of a natural kneejoint with a knee prosthesis and pertains, more specifically, to achieving an extended range of motion with reduced contact stresses within the components of the knee prosthesis and concomitant improved articular performance, together with greater longevity.

During articulation of a natural kneejoint, flexion between the tibia and the femur takes place about a transverse axis while, at the same time, some relative rotation between the tibia and the femur occurs about a longitudinal axis. Such flexion and rotation is necessary to carry out a normal gate cycle. In addition, the femur experiences posterior rollback, that is, a combination of backward rolling and sliding of the distal femur along the proximal tibia as the knee flexes. Stability of the knee, during flexion and extension, depends, in part, upon the action of the cruciate ligaments and the collateral ligaments. During extension, the collateral ligaments tighten, while during flexion the collateral ligaments loosen to enable articulation of the femur and tibia to be accompanied by posterior rollback and internal tibia rotation, allowing deep flexion of the knee joint, that is, flexion in the range of approximately 110° to 150° of flexion.

2. Description of the Related Prior Art

Currently available knee prostheses utilize femoral components having posterior condyles which provide a maximum coverage of the distal femur. Rather than mimicking the natural posterior condyle shape and length, the posterior condyles of a femoral component of such knee prostheses is lengthened relative to the length of the natural posterior condyles. The extended length often prevents loosening of the collateral ligaments, as seen in the natural knee during flexion, resulting in a tight knee with a reduced range of flexion.

Additionally, current knee prostheses do not allow for anatomically accurate rotation about the longitudinal axis in deep flexion. In deep flexion, the condylar surfaces of the femoral component are forced against the counterpart articular surfaces of the tibial component, lifting the femoral component from the tibial component as rotational forces are increased, with the result that the knee becomes distracted and excessive wear is generated in the tibial component. Further, by virtue of the relative contours of the condylar surfaces and the articular surfaces, the posterior condyles of current knee prostheses operate to reduce contact area in deep flexion, causing increased contact stress with concomitant increased wear in the tibial component. Similarly, the relative contours of the condylar surfaces and the articular surfaces tend to reduce the range of hyperextension, tend to cause distraction of the knee as hyperextension is increased, and engenders higher contact stress as hyperextension is increased, resulting in excessive wear in the tibial component.

BRIEF SUMMARY OF THE INVENTION

The present invention provides an improvement which alleviates the above-outlined problems and enables a wider range of motion, both in flexion and in hyperextension. As such, the present invention attains several objects and advantages, some of which are summarized as follows: Enables articulation in a knee prosthesis to follow better the anatomical range of motion of a natural knee, through a range which includes deep flexion and increased hyperextension, without excessive stress placed upon the engaged condylar and articular surfaces of the femoral and tibial components of the knee prosthesis, while militating against distraction of the femoral and tibial components 0 during deep flexion and increased hyperextension; extends the range of motion in a knee prosthesis while reducing contact stresses, and concomitant wear, as articulation approaches maximum flexion and hyperextension; allows a wide range of articulation accompanied by more anatomically accurate rotation about a longitudinal axis for better performance in a prosthetic knee; avoids unwanted distraction of the knee during deep flexion and during increased hyperextension; offers a recipient of a knee prosthesis a greater range of motion with increased ease and comfort; reduces wear and increases longevity in a knee prosthesis; provides a knee prosthesis with exemplary performance over an extended service life.

The above objects and advantages are attained by the present invention which may be described briefly as providing, in a knee prosthesis for implantation to replace a natural knee joint, the knee prosthesis having a femoral component including at least one condylar element with a condylar surface having a transverse axis of rotation, and a tibial component including at least one articular surface configured for engagement with the condylar surface of the femoral component during articulation of the knee prosthesis about the transverse axis of rotation, with the condylar surface and the articular surface engaged along corresponding posterior aspects during deep flexion, and along corresponding anterior aspects during hyperextension, the condylar surface and the articular surface being configured for enabling engagement between the condylar surface and the articular surface along a prescribed, track having a predetermined curvature which enables relative rotational movement between the femoral component and the tibial component about a longitudinal axis of rotation during articulation about the transverse axis of rotation, the condylar surface and the articular surface including profile contour configurations in generally medial-lateral longitudinal planes, the condylar surface having an inner surface portion confronting the longitudinal axis of rotation, and the articular surface having an outer surface portion for engagement with the inner surface portion during articulation, an improvement wherein at least one of the inner surface portion and the outer surface portion is flared in a direction away from a corresponding other of the inner surface portion and the outer surface portion, along the posterior aspect of a corresponding one of the condylar surface and the articular surface so as to maintain essential congruency between the profile contour configurations and thereby enable an increased area of contact and decreased stress between the condylar surface and the articular surface while militating against distraction of the knee prosthesis during articulation through deep flexion.

In addition, the present invention provides, in a knee prosthesis for implantation to replace a natural kneejoint, the knee prosthesis having a femoral component including at least one condylar element with a condylar surface having a transverse axis of rotation, and a tibial component including at least one articular surface configured for engagement with the condylar surface of the femoral component during articulation of the knee prosthesis about the transverse axis of rotation, with the condylar surface and the articular surface engaged along corresponding posterior aspects during flexion, and along corresponding anterior aspects during hyperextension, the condylar surface and the articular surface being configured for enabling engagement between the condylar surface and the articular surface along a prescribed track having a predetermined curvature which enables relative rotational movement between the femoral component and the tibial component about a longitudinal axis of rotation during articulation about the transverse axis of rotation, the condylar surface and the articular surface including profile contour configurations in generally medial-lateral longitudinal planes, the condylar surface having an inner surface portion confronting the longitudinal axis of rotation, and the articular surface having an outer surface portion for engagement with the inner surface portion during articulation, an improvement wherein at least one of the inner surface portion and the outer surface portion is flared in a direction away from a corresponding other of the inner surface portion and the outer surface portion, along the anterior aspect of at least a corresponding one of the condylar surface and the articular surface so as to maintain essential congruency between the profile contour configurations and thereby enable an increased area of contact and decreased stress between the condylar surface and the articular surface while militating against distraction of the knee prosthesis during articulation through hyperextension.

Further, the present invention provides, in a knee prosthesis for implantation to replace a natural knee joint, the knee prosthesis having a femoral component including a lateral condylar element and a medial condylar element, each condylar element including a condylar surface having a transverse axis of rotation, and a tibial component including a lateral articular surface and a medial articular surface, each articular surface being configured for engagement with a corresponding condylar surface of the femoral component during articulation of the knee prosthesis about the transverse axis of rotation, with the condylar surfaces and the articular surfaces engaged along corresponding posterior aspects during deep flexion, and along corresponding anterior aspects during hyperextension, each condylar surface and each articular surface being configured for enabling engagement between the condylar surfaces and corresponding articular surfaces along respective prescribed tracks each having a predetermined curvature which enable relative rotational movement between the femoral component and the tibial component about a longitudinal axis of rotation during articulation about the transverse axis of rotation, the condylar surfaces and the articular surfaces including profile contour configurations in generally medial-lateral longitudinal planes, the condylar surfaces each having an inner surface portion confronting the longitudinal axis of rotation and the articular surfaces each having an outer surface portion for engagement with a corresponding inner surface portion during articulation, an improvement wherein at least one of the inner surface portions and the outer surface portions is flared in a direction away from a corresponding other of the inner surface portions and the outer surface portions, along the posterior aspect of at least a corresponding one of the condylar surfaces and articular surfaces so as to maintain essential congruency between the profile contour configurations and thereby enable an increased area of contact and decreased stress between the condylar surfaces and the articular surfaces while militating against distraction of the knee prosthesis during articulation through deep flexion.

Still further, the present invention provides, in a knee prosthesis for implantation to replace a natural knee joint, the knee prosthesis having a femoral component including a lateral condylar element and a medial condylar element, each condylar element including a condylar surface having a transverse axis of rotation, and a tibial component including a lateral articular surface and a medial articular surface, each articular surface being configured for engagement with a corresponding condylar surface of the femoral component during articulation of the knee prosthesis about the transverse axis of rotation, with the condylar surfaces and the articular surfaces engaged along corresponding posterior aspects during flexion, and along corresponding anterior aspects during hyperextension, each condylar surface and each articular surface being configured for enabling engagement between the condylar surfaces and corresponding articular surfaces along respective prescribed tracks each having a predetermined curvature which enables relative rotational movement between the femoral component and the tibial component about a longitudinal axis of rotation during articulation about the transverse axis of rotation, the condylar surfaces and the articular surfaces including profile contour configurations in generally medial-lateral longitudinal planes, the condylar surfaces each having an inner surface portion confronting the longitudinal axis of rotation and the articular surfaces each having an outer surface portion for engagement with a corresponding inner surface portion during articulation, an improvement wherein at least one of the inner surface portions and the outer surface portions is flared, in a direction away from a corresponding other of the inner surface portions and the outer surface portions, along the anterior aspect of at least a corresponding one of the condylar surfaces and articular surfaces so as to maintain essential congruency between the profile contour configurations and thereby enable an increased area of contact and decreased stress between the condylar surfaces and the articular surfaces while militating against distraction of the knee prosthesis during articulation through hyperextension.

BRIEF DESCRIPTION OF THE SEVERAL VIEWS OF THE DRAWING

The invention will be understood more fully, while still further objects and advantages will become apparent, in the following detailed description of a preferred embodiment of the invention illustrated in the accompanying drawing, in which.

DETAILED DESCRIPTION OF THE INVENTION

Figures 1, 2:
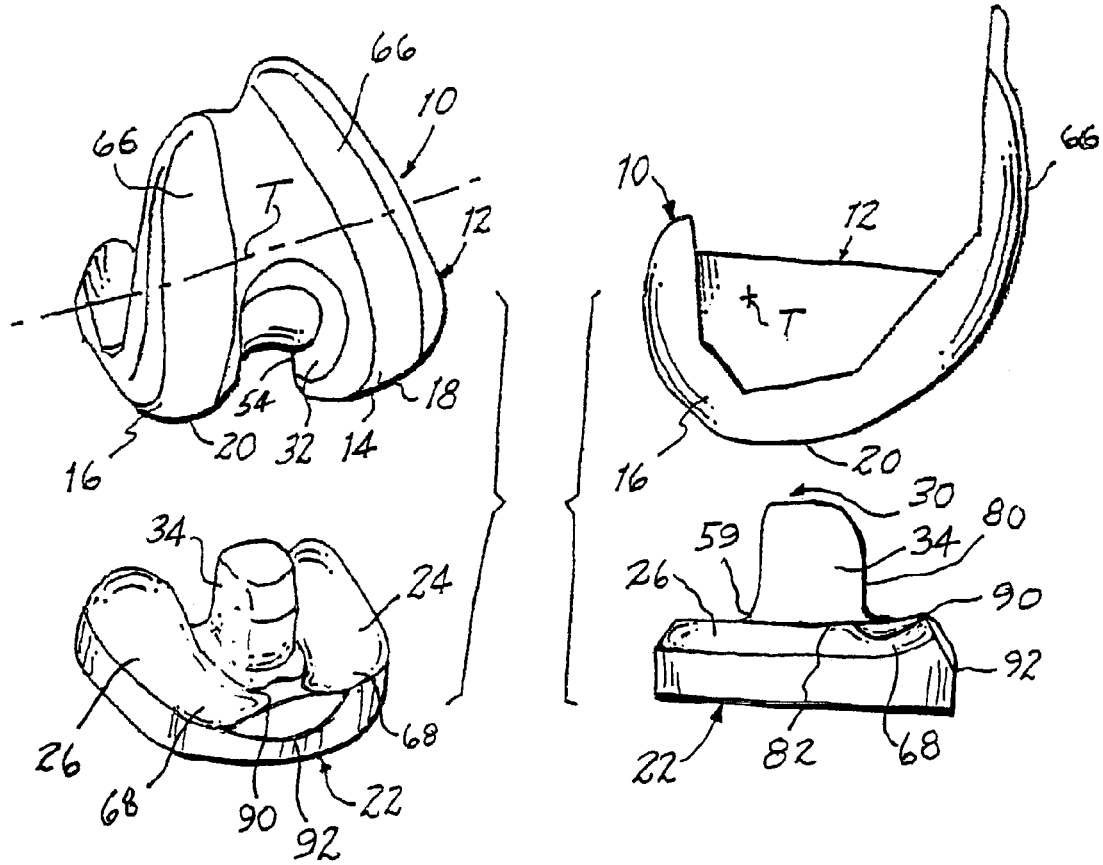
FIG. 1 is an exploded perspective view showing portions of a knee prosthesis constructed in accordance with the present invention.
FIG. 2 is an exploded side elevational view of the portions of the knee prosthesis.

Referring now to the drawing, and especially to FIGS. 1 and 2 thereof, a knee prosthesis constructed in accordance with the present invention is shown at 10 and is seen to comprise a femoral component 12 having condylar elements illustrated in the form of condyles including a lateral condyle 14 and a medial condyle 16. Each condyle 14 and 16 includes a condylar surface 18 and 20, respectively. A tibial component 22 has articular surfaces including a lateral articular surface 24 for engagement with lateral condylar surface 18 of lateral condyle 14, and a medial articular surface 26 for engagement with medial condylar surface 20 of medial condyle 16, for rotation about a transverse axis of rotation T.

In the total knee replacement provided by knee prosthesis 10, both the anterior and the posterior cruciate ligaments are sacrificed, and knee prosthesis 10 includes a stabilizing mechanism 30 for stabilizing the engagement between the lateral condyle 14 and the lateral articular surface 24, and between the medial condyle 16 and the medial articular surface 26, during articulation of the knee prosthesis 10 within the range of articulation in which the posterior cruciate ligament ordinarily would provide stability in the natural knee. Stabilizing mechanism 30 includes a stabilizing compartment 32 on the femoral component 12, between the condyles of the femoral component 12, the compartment 32 preferably being located intermediate the lateral condyle 14 and the medial condyle 16 of the femoral component 12, and a stabilizing post 34 on the tibial component 22, between the articular surfaces of the tibial component 22, the post 34 preferably being located intermediate the lateral articular surface 24 and the medial articular surface 26 of the tibial component 22, for projecting in a superior direction into the stabilizing compartment 32, in a manner known in posterior stabilized prosthetic knee implants.

Figure 3:
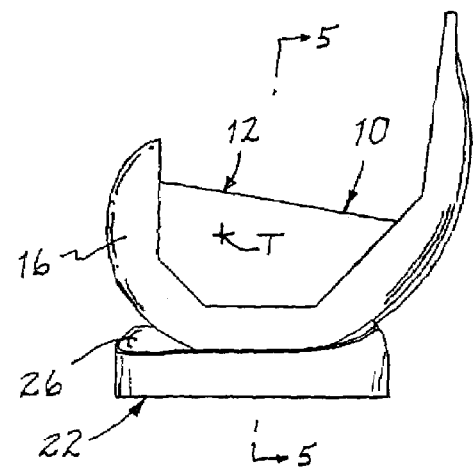
FIG. 3 is a side elevational view of the portions of the knee prosthesis showing the femoral component engaged with the tibial component, at 0° of flexion.
Figure 4:
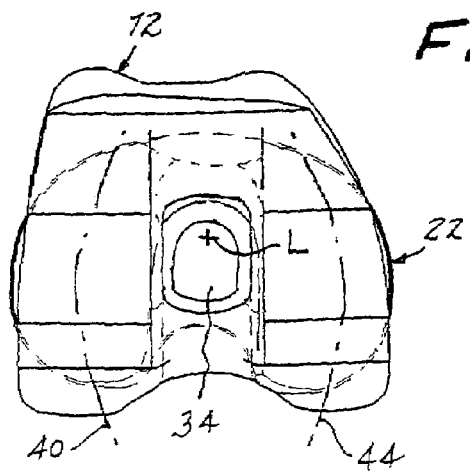
FIG. 4 is a partially diagrammatic top plan view of the prosthesis in the position shown in FIG. 3.
Figure 5:
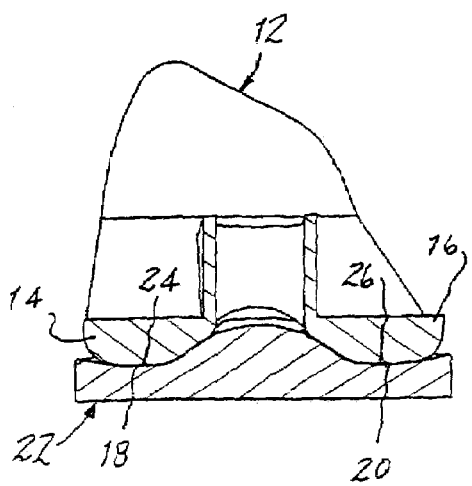
FIG. 5 is a cross-sectional view taken along line 5—5 of FIG. 3.
Figure 6:
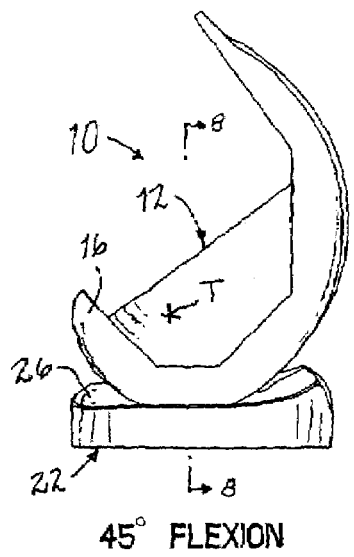
FIGS. 6, 7 and 8 are views similar to FIGS. 3, 4 and 5, respectively, but showing the components at 45° of flexion.
Figure 7:
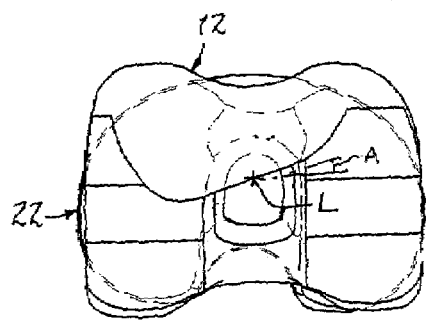
Figure 8:
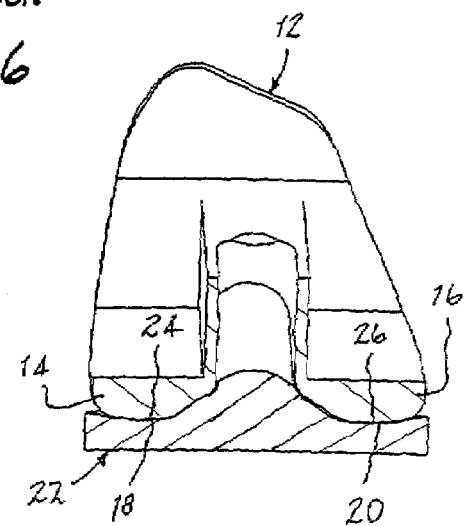
Figure 9:
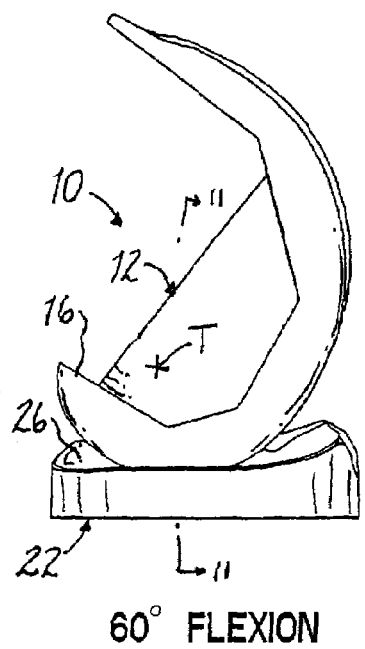
FIGS. 9, 10 and 11 are views similar to FIGS. 6, 7 and 8, respectively, but showing the components at 60° of flexion.
Figure 10:
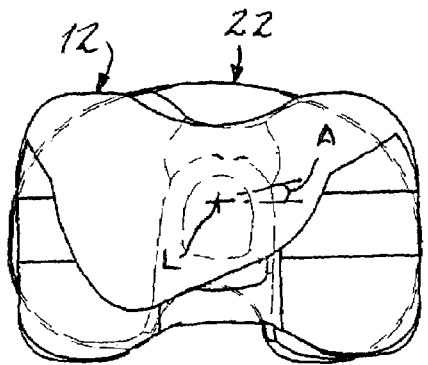
Figure 11:
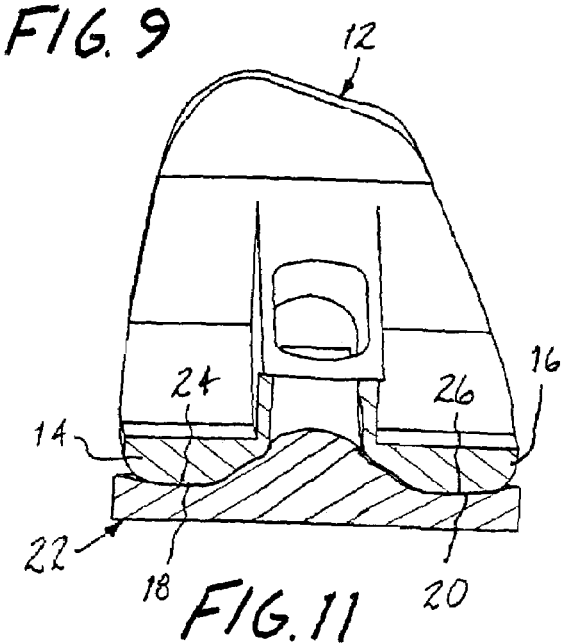
Figure 12:
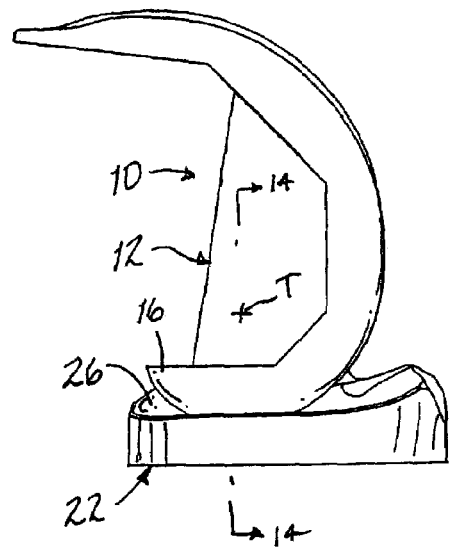
FIGS. 12, 13 and 14 are views similar to FIGS. 6, 7 and 8, respectively, but showing the components at 90° of flexion.
Figure 13:
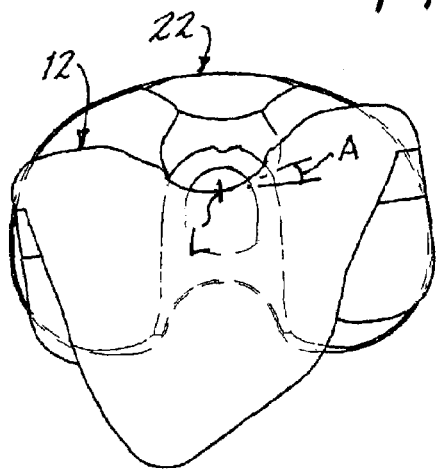
Figure 14:
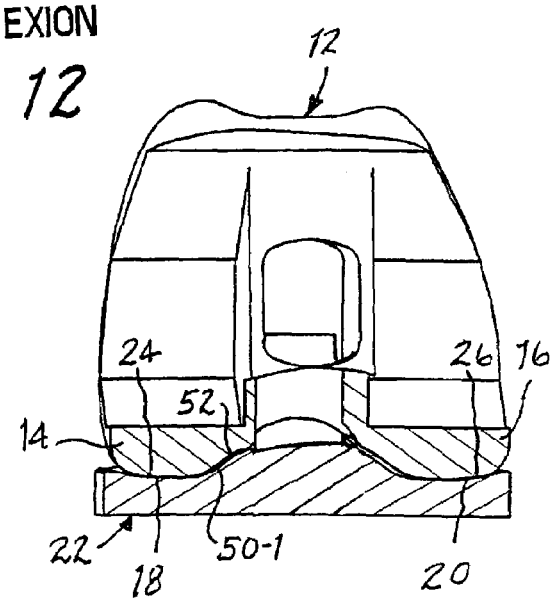
Figure 15:
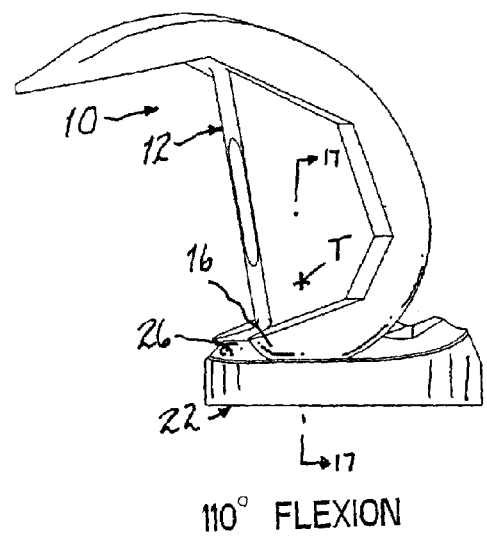
FIGS. 15, 16 and 17 are views similar to FIGS. 6, 7 and 8, respectively, but showing the components at 110° of flexion.
Figure 16:
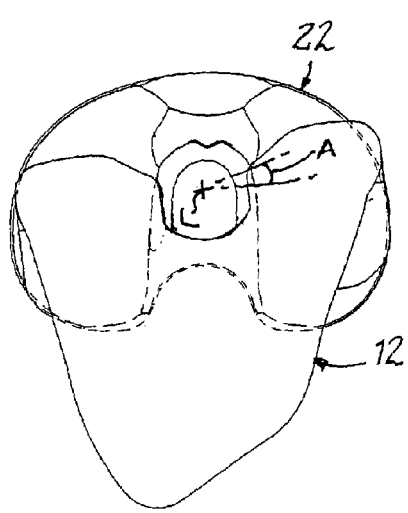
Figure 17:
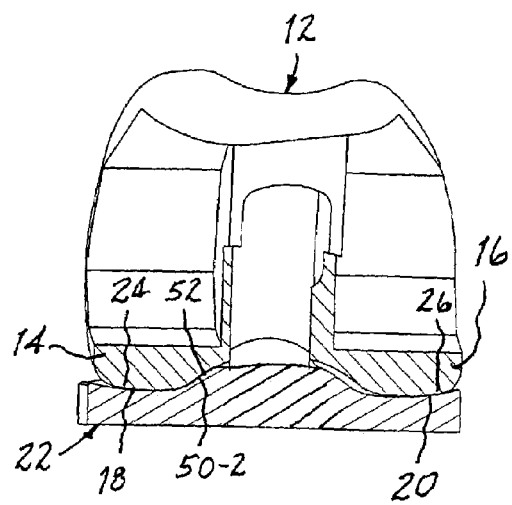
Figure 18:
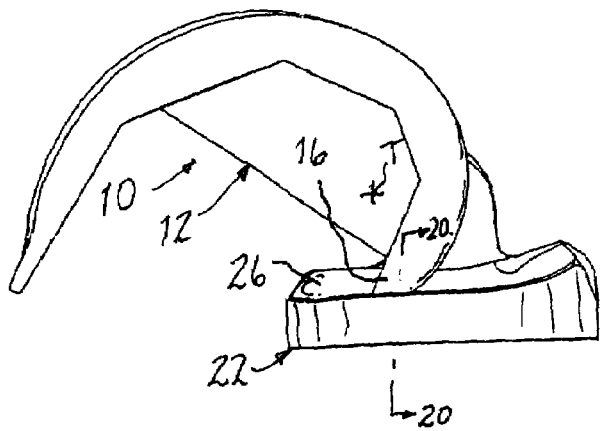
FIGS. 18, 19 and 20 are views similar to FIGS. 6, 7 and 8, respectively, but showing the components at 150° of flexion.
Figure 19:
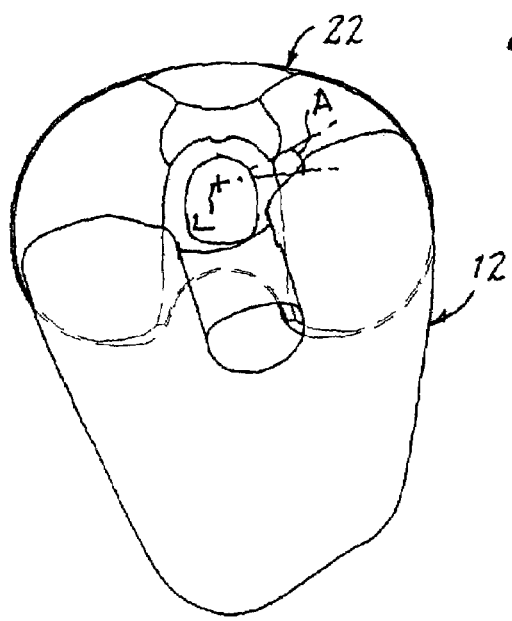
Figure 20:
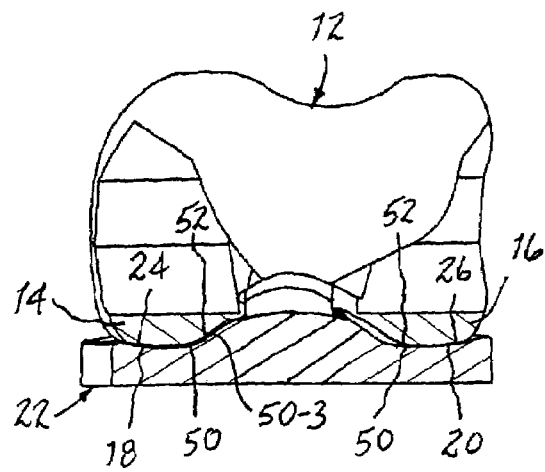
Figure 21:
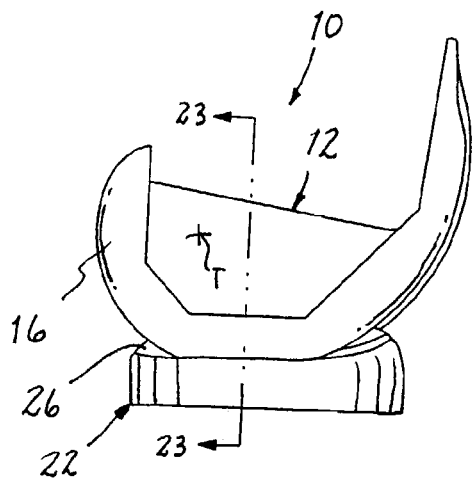
FIGS. 21, 22 and 23 are views similar to FIGS. 3, 4 and 5, respectively, but showing the components about to articulate into hyperextension.
Figure 22:
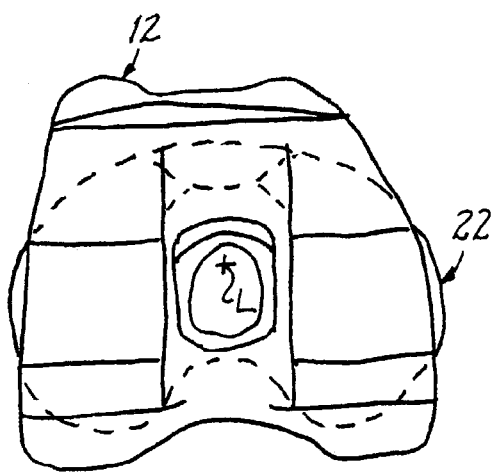
Figure 23:
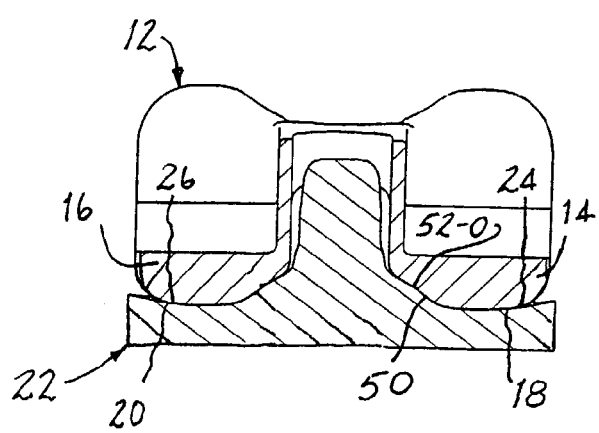
Figure 24:
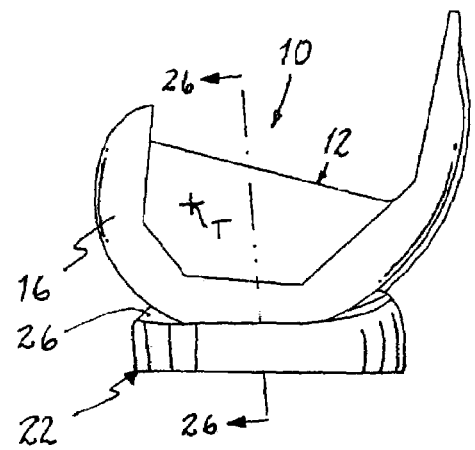
FIGS. 24, 25 and 26 are views similar to FIGS. 21, 22 and 23, respectively, but showing the components at 4° of hyperextension.
Figure 25:
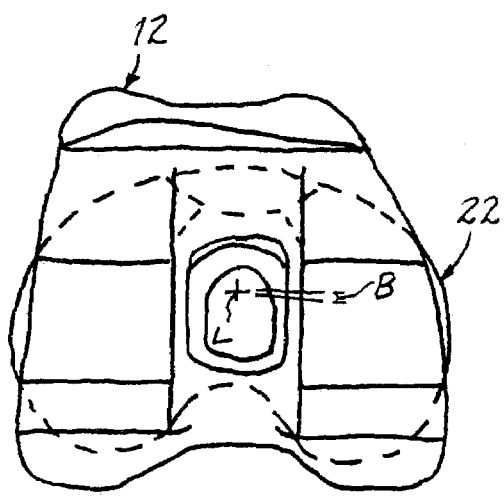
Figure 26:
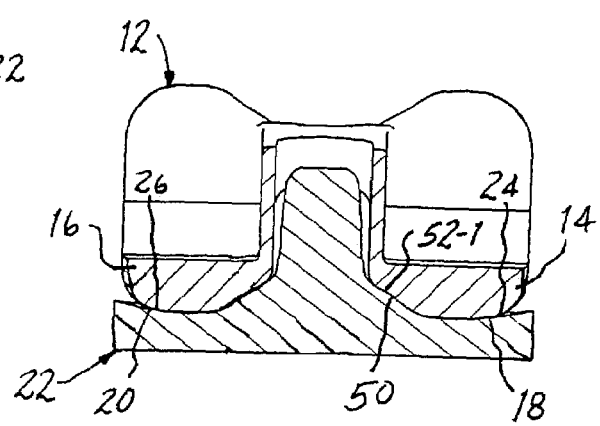
Figure 27:
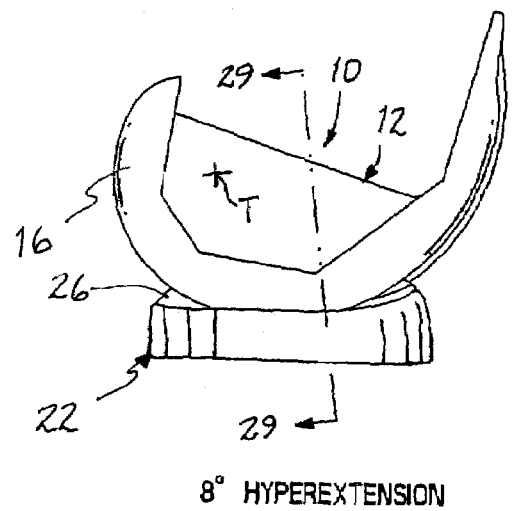
FIGS. 27, 28 and 29 are views similar to FIGS. 21, 22 and 23, respectively, but showing the components at 8° of hyperextension.
Figure 28:
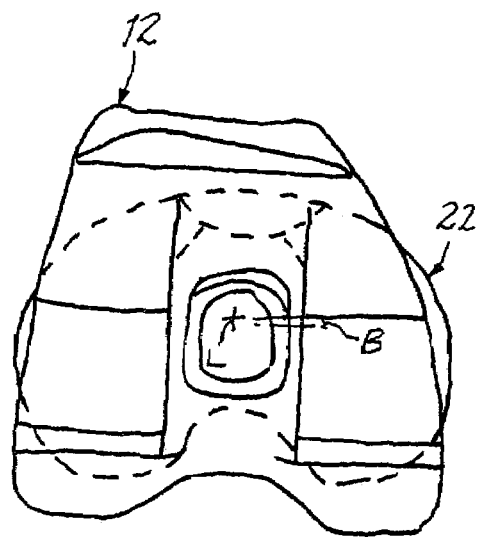
Figure 29:
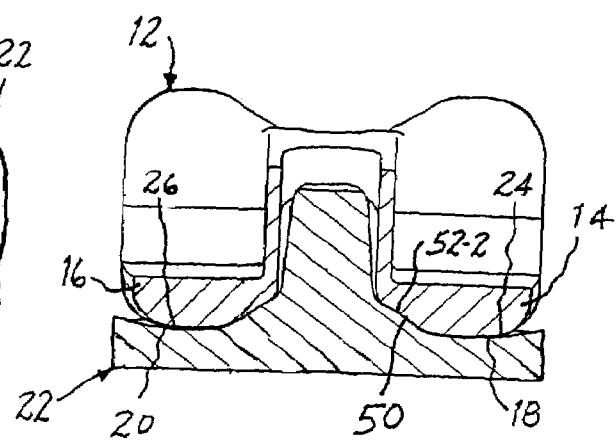
Figure 30:
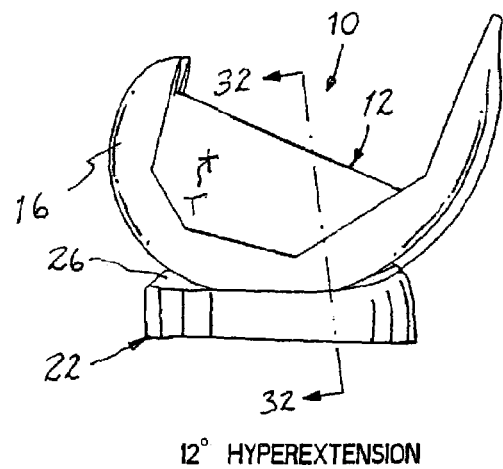
FIGS. 30, 31 and 32 are views similar to FIGS. 21, 22 and 23, respectively, but showing the components at 12° of hyperextension.
Figure 31:
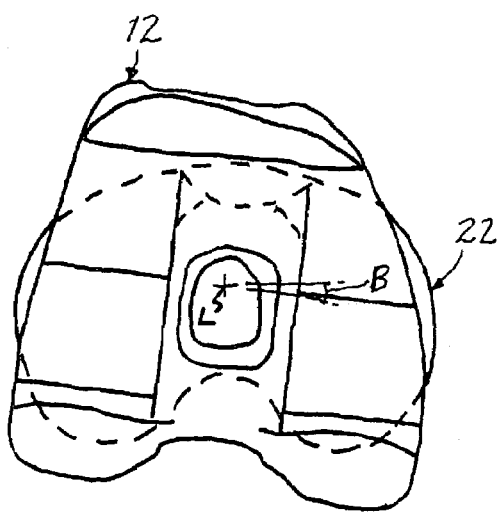
Figure 32:
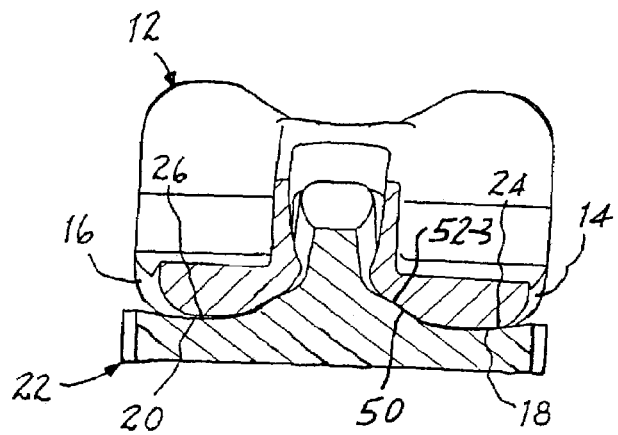

Turning now to FIGS. 3 through 5, viewed in conjunction with FIGS. 30 and 31, knee prosthesis 10 is illustrated at 0' of flexion, and the condylar surfaces of the condyles of the femoral component 12 are engaged with the articular surfaces of the tibial component 22. The condylar surfaces 18 and 20 and the articular surfaces 24 and 26 are configured such that upon implantation of the knee prosthesis 10, relative rotational movement between the femoral component 12 and the tibial component 22 during articulation of the knee prosthesis 10 better emulates the relative rotation observed in the natural knee. Thus, engagement between lateral condylar surface 18 and lateral articular surface 24 is so complementary, and preferably essentially congruent, as illustrated in FIG. 5 by the profile contour configurations in a generally medial-lateral longitudinal plane at positions along a first prescribed track 40 having a predetermined curvature in a generally coronal plane, and engagement between medial condylar surface 20 and medial articular surface 26 is so complementary, and preferably essentially congruent, as illustrated in FIG. 5, along a second prescribed track 44 having a predetermined curvature in a generally coronal plane, that the relative configurations of the condylar surfaces 18 and 20 and the articular surfaces 24 and 26 will enable relative rotational movement between the femoral component 12 and the tibial component 22, about a longitudinal axis L, lying in a generally sagittal plane, in such a manner as to emulate the relative rotation observed in the natural knee during articulation about transverse axis of rotation T. In the preferred construction, tracks 40 and 44 each have a generally arcuate curvature.

FIGS. 6 through 20, together with FIGS. 3 through 5, illustrate articulation of the knee prosthesis 10 in a range of flexion from 0° of flexion to 150° of flexion. During flexion within a range of about 0° flexion to 110° of flexion, relative rotation between the femoral component 12 and the tibial component 22 takes place about longitudinal axis L. The total relative rotation at 110° of flexion is about 9°, and is illustrated in increments depicted by an angle A in each of FIGS. 7, 10, 13, 16 and 19, angle A denoting about 4.5° of relative rotation at 45° of flexion, about 5° of relative rotation at 60° of flexion, and about 8° of relative rotation at 90° of flexion, until about 9° of relative rotation is reached at 110° of flexion. Throughout flexion and extension within that range of about 0° of flexion and about 110° of flexion engagement between lateral condylar surface 18 and lateral articular surface 24 is along track 40 and the relative profile contour configurations maintain the desired essential congruency between the engaged surfaces 18 and 24. Likewise, engagement between the medial condylar surface 20 and the medial articular surface 26 is along track 44 and essential congruency is maintained between the engaged surfaces 20 and 26. The essential congruency assures that contact between the condylar surfaces and the respective articular surfaces is maintained over a maximum area of contact so as to minimize contact stresses and reduce wear on the tibial component 22.

Figure 33:
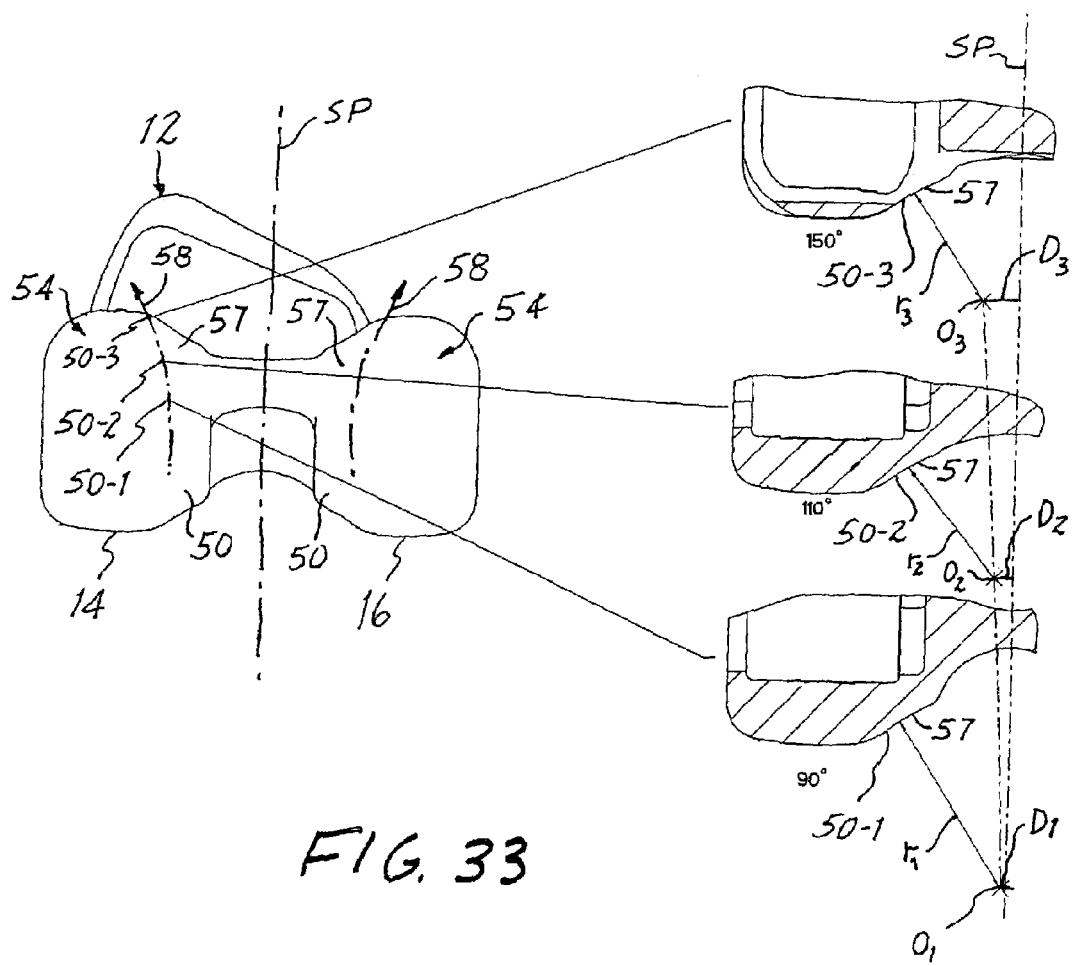
FIG. 33 is an enlarged posterior elevational view showing a posterior aspect of condylar surfaces of the femoral component of the knee prosthesis, together with cross-sectional views taken in generally medial-lateral planes at locations corresponding to about 90°, 110° and 150° of flexion along a condylar surface and showing profile contour configurations at those locations.

In order to maintain the desired congruency upon flexion beyond the range of about 0° of flexion and 110° of flexion, and enable deep flexion, up to about 150° of flexion, while allowing more anatomically accurate relative rotation about longitudinal axis L and deterring unwanted distraction of the knee prosthesis 10, the profile contour configurations of the condylar surfaces 18 and 20 are further configured to assure the desired congruency and to militate against distraction of the knee prosthesis 10. Thus, each condylar surface 18 and 20 includes an inner surface portion 50 which engages a corresponding outer surface portion 52 of a respective articular surface 24 and 26 along corresponding posterior aspects 54 and 56 of the respective inner and outer surface portions 50 and 52, and the inner surface portions 50 are flared outwardly in directions away from corresponding outer surface portions 52. As illustrated diagrammatically in FIG. 33, a flared surface area 57 extends along each inner surface portion 50 and follows a direction 58 diverging outwardly relative to an intermediate sagittal plane SP so as to maintain essential congruency between the profile contour configurations, along the posterior aspects 54 and 56 of the condylar surfaces 18 and 20 and the corresponding articular surfaces 24 and 26. The profile contour configuration of the flared surface area 57 of an inner surface portion 50 is depicted by 50-1 at a location corresponding to 90° of flexion, by 50-2 at a location corresponding to 110° of flexion, and by 50-3 at a location corresponding to 150° of flexion. Each profile contour configuration 50-1, 50-2, and 50-3 has a corresponding radius $r_1$, $r_2$ and $r_3$ extending from a respective origin $O_1$, $O_2$ and $O_3$ spaced outwardly from sagittal plane SP a corresponding distance $D_1$, $D_2$ and $D_3$. Distance $D_2$ is greater than distance $D_1$, and distance $D_3$ is greater than distance $D_2$ so as to accomplish the desired outward flare of the surface area 57. The term "flared", as applied to each inner surface portion 50, is meant to describe a smooth and gradual transition as the inner surface portion 50 follows the direction 58 of surface area 57, as represented in FIG. 33 wherein the origins of the radii of profile contour configurations 50-1, 50-2 and 50-3 are spaced successively farther outwardly from sagittal plane SP so as to maintain the desired congruence between the condylar and articular surfaces and avoid unwanted distraction of the knee prosthesis 10 during articulation in deep flexion. As illustrated in FIG. 33, the outward flare of the inner surface portions 50 preferably commences at locations on condylar surfaces 18 and 20 corresponding to about 90° of flexion and extends to locations corresponding to about 150° of flexion to enable relative rotation between the femoral component 12 and the tibial component 22 to continue to about 12° to 15° of rotation at 150° of flexion while maintaining a maximum area of contact between the respective condylar and articular surfaces for minimizing contact stresses and reducing wear on the tibial component 22. In addition, the flared configuration of inner surface portions 50 enables deep flexion to take place without deleterious elevation of the transverse axis of rotation T of the condylar surfaces 18 and 20, and concomitant unwanted distraction of the knee prosthesis 10 which could result in tightening of the knee. Further, the flared configuration provided along the posterior aspects 54 of the inner surface portions 50 assures that contact between the femoral component 12 and the stabilizer post 34 during deep flexion occurs nearer the basal aspect 59 of the post 34, thereby minimizing stress placed on the post 34 by such contact. It is noted that a similar result can be attained by flaring the outer surface portions 52 inwardly, in directions away from corresponding inner surface portions 50, inwardly toward sagittal plane SP; however, by flaring the inner surface portions 50 outwardly, rather than flaring the outer surface portions 52 inwardly, deletion of bearing material from tibial component 22 is avoided so that bearing material of the tibial component 22 is conserved and maintained at a maximum, with a concomitant increase in longevity.

In the preferred construction, the profile contour configurations at 50-1, 50-2 and 50-3 of the inner surface portions 50 are provided with a concave contour along the posterior aspect 54 of the condylar surfaces 18 and 20, as illustrated by the radii of the profile contour configurations, while the outer surface portions 52 are provided with an essentially complementary convex contour along the posterior aspects 56 of the articular surfaces 24 and 26 so as to assure increased areas of contact without decreasing the amount of bearing material available to the tibial component 22 at the articular surfaces 24 and 26.

Figure 34:
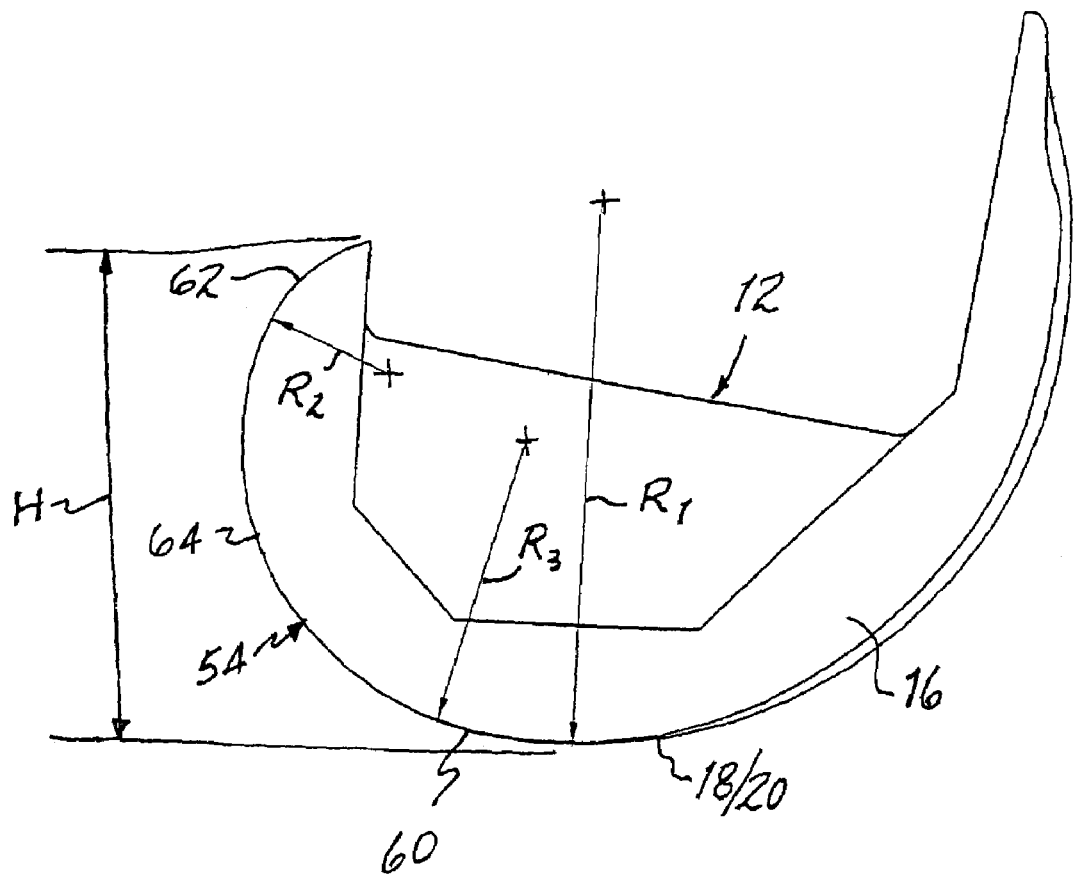
FIG. 34 is an enlarged diagrammatic side elevational view of the femoral component of the knee prosthesis.

Deep flexion is further facilitated by modifying the radius of curvature of the condylar surfaces 18 and 20. As best seen in FIG. 34, the posterior aspect 54 of each condylar surface 18 and 20 is divided into portions having differing prescribed radii of curvature. Thus, the portions 60 of condylar surfaces 18 and 20 engaged by corresponding articular surfaces 24 and 26 during flexion from 0° of flexion to about 10° of flexion includes a radius of curvature $R_1$ of a prescribed dimension. The posterior portions 62 of condylar surfaces 18 and 20, engaged by corresponding articular surfaces 24 and 26 beyond about 110° of flexion, follow a radius of curvature $R_2$ which is considerably smaller than radius of curvature $R_1$. The intermediate portions 64 of condylar surfaces 18 and 20, engaged by corresponding articular surfaces 24 and 26 between about 10° of flexion and 110° of flexion, follow an intermediate radius of curvature $R_3$ such that intermediate portions 64 are tangent to portions 60 and 62 to assure a smooth transition along portions 60, 64 and 62. As a result, the overall height H of the condyles 14 and 16 is reduced and the transverse axis of rotation T of condylar surfaces 18 and 20 does not become elevated, that is, does not move in a superior direction away from the tibial component 22, as the knee prosthesis 10 is articulated into deep flexion, as illustrated in FIGS. 12 through 20, and unwanted distraction of the knee prosthesis 10, and concomitant tightening of the knee, is avoided, thereby assuring ease of entry fully into deep flexion, with reduced contact forces between the condylar surfaces 18 and 20 and corresponding articular surfaces 24 and 26. The combination of the reduced contact forces and the increased area of contact between the inner and outer surface portions 50 and 52 enables reduced stresses and concomitant reduced wear, together with increased longevity.

Figure 35:
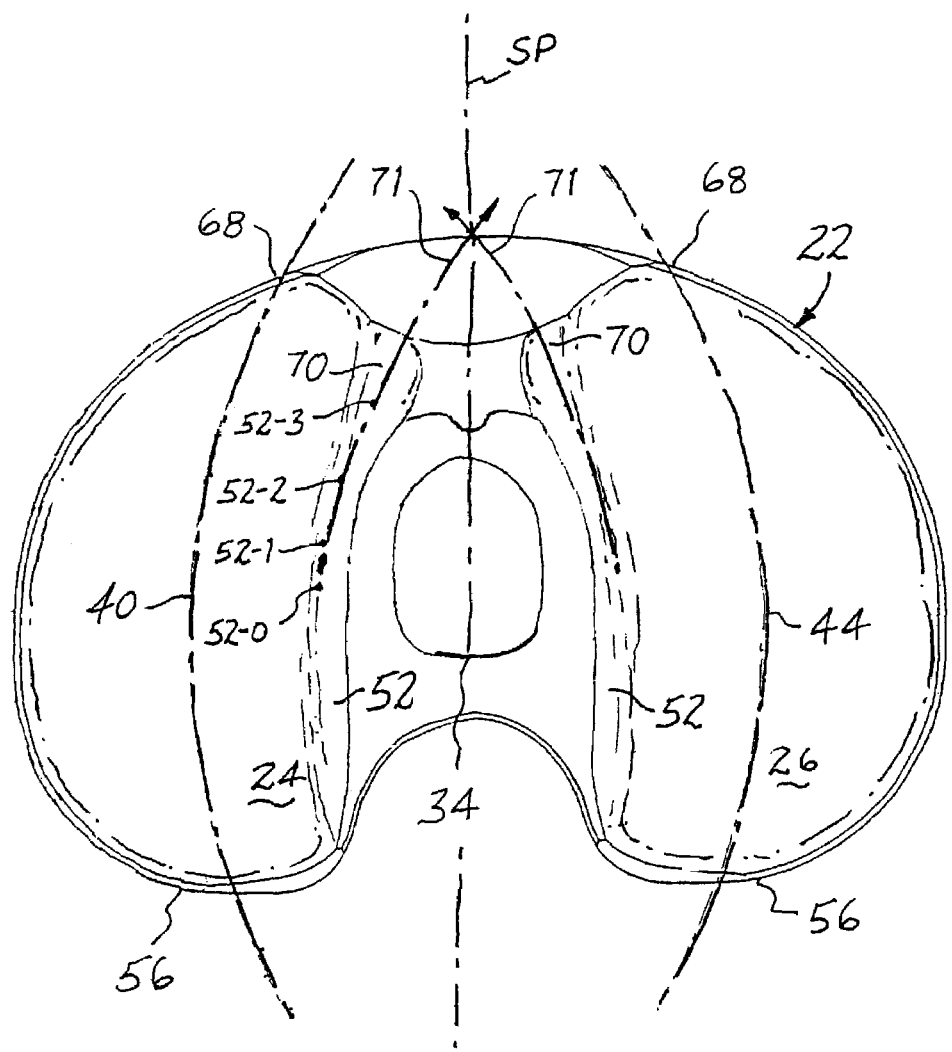
FIG. 35 is an enlarged diagrammatic top plan view showing the articular surfaces of the tibial component of the knee prosthesis.

Referring now to FIGS. 21 through 32, viewed in conjunction with FIG. 35, the range of hyperextension is increased to accommodate increased hyperextension up to about 12° of hyperextension, together with relative rotation between the femoral component 12 and the tibial component 22 of up to about 3° to 6° of relative rotation about longitudinal axis L. As seen in FIG. 35, the outer surface portions 52 of articular surfaces 24 and 26 are flared inwardly in a direction away from corresponding inner surface portions 50 of condylar surfaces 18 and 20. As illustrated diagrammatically in FIG. 35, a flared surface area 70 extends along each outer surface portion 52 and follows a direction 71 converging inwardly relative to sagittal plane SP so as to maintain essential congruency between the profile contour configurations, along anterior aspects 66 and 68 of the condylar surfaces 18 and 20 and the corresponding articular surfaces 24 and 26. The term "flared", as applied to each outer surface portion 52, is meant to describe a smooth and gradual transition of the outer surface portion 52 as the outer surface portion 52 follows the direction 71 of surface area 70, as seen in FIGS. 23, 26, 29 and 32 wherein profile contour configurations at 52-0, 52-1, 52-2 and 52-3, at locations along outer surface portion 52, are spaced successively closer to sagittal plane SP, in a manner analogous to that described above in connection with the successive spacing of profile contour configurations located along inner surface portions 50 so as to maintain the desired congruence between corresponding condylar and articular surfaces and to militate against distraction of the knee prosthesis 10 during articulation in hyperextension. The inward flare of the outer surface portions 52 preferably commences at locations on the articular surfaces 24 and 26 corresponding to about 0° of flexion and extends to locations corresponding to about 12° of hyperextension to enable relative rotation between the femoral component 12 and the tibial component 22, as depicted by angle B in FIGS. 25, 28 and 31, to continue up to about 3° to 6° of rotation at the extended hyperextension of about 12° of hyperextension while maintaining a maximum area of contact between the respective condylar and articular surfaces for minimizing contact stresses and reducing wear on the tibial component 22. In addition, the flared configuration provided along the anterior aspect 68 of the articular surfaces 24 and 26 assures that any contact between the femoral component 12 and the anterior aspect 80 of the stabilizing post 34 occurs nearer the base 82 of the post 34, thereby minimizing any stress placed on the post 34 by such contact. It is noted that a similar result could be attained by flaring the inner surface portions 50 outwardly in directions away from corresponding outer surface portions 52, diverging outwardly away from sagittal plane SP; however, by flaring the outer surface portions 52 inwardly, along anterior aspects 68, rather than flaring the inner surface portions 50 outwardly, along anterior aspects 66, material of the femoral component 12 is conserved and an appropriate patellar track is maintained along the anterior aspect of the femoral component 12.

In the preferred construction, the inner surface portions 50 are provided with a concave contour along the anterior aspect 66 of the condylar surfaces 18 and 20, while the outer surface portions 52 are provided with an essentially complementary convex contour along the anterior aspect 68 of the articular surfaces 24 and 26 so as to assure increased areas of contact without decreasing the amount of bearing material available at the articular surfaces 24 and 26.

Returning briefly to FIGS. 1 and 2, viewed in connection with FIG. 35, the inward convergence of prescribed tracks 40 and 44 along the anterior aspects 68 of articular surfaces 26 is accompanied by an elevation of the tracks 40 and 44 along the anterior aspects 68, so that sufficient bearing material is available at the anterior aspects 68 to enable the inward flaring of the outer surface portions 52 without a deleterious loss of bearing material in the tibial component 22. Further, the inward convergence of tracks 40 and 44 along the anterior aspects 68 provides for a raised edge 90 adjacent the anterior boundary 92 of the tibial component 22, which raised edge 90 assists in maintaining the desired engagement between the femoral component 12 and the tibial component 22 during articulation in hyperextension.

It will be seen that the present invention attains all of the objects and advantages summarized above, namely: Enables articulation in a knee prosthesis to follow better the anatomical range of motion of a natural knee, through a range which includes deep flexion and increased hyperextension, without excessive stress placed upon the engaged condylar and articular surfaces of the femoral and tibial components of the knee prosthesis, while militating against distraction of the femoral and tibial components during deep flexion and increased hyperextension; extends the range of motion in a knee prosthesis while reducing contact stresses, and concomitant wear, as articulation approaches maximum flexion and hyperextension; allows a wide range of articulation accompanied by more anatomically accurate rotation about a longitudinal axis for better performance in a prosthetic knee; avoids unwanted distraction of the knee during deep flexion and during increased hyperextension; offers a recipient of a knee prosthesis a greater range of motion with increased ease and comfort; reduces wear and increases longevity in a knee prosthesis; provides a knee prosthesis with exemplary performance over an extended service life.

It is to be understood that the above detailed description of a preferred embodiment of the invention is provided by way of example only. Various details of design and construction may be modified without departing from the true spirit and scope of the invention, as set forth in the appended claims.

The invention claimed is:

1. In a knee prosthesis for implantation to replace a natural knee joint, the knee prosthesis having a femoral component including at least one condylar element with a condylar surface having a transverse axis of rotation, and a tibial component including at least one articular surface configured for engagement with the condylar surface of the femoral component during articulation of the knee prosthesis about the transverse axis of rotation, with the condylar surface and the articular surface engaged along corresponding posterior aspects during deep flexion, and along corresponding anterior aspects during hyperextension, the condylar surface and the articular surface being configured for enabling engagement between the condylar surface and the articular surface along a prescribed track having a predetermined curvature which enables relative rotational movement between the femoral component and the tibial component about a longitudinal axis of rotation during articulation about the transverse axis of rotation, the condylar surface and the articular surface including profile contour configurations in generally medial-lateral longitudinal planes, the condylar surface having an inner surface portion confronting the longitudinal axis of rotation, and the articular surface having an outer surface portion for engagement with the inner surface portion during articulation:

an improvement wherein at least one of the inner surface portion and the outer surface portion is flared in a direction away from a corresponding other of the inner surface portion and the outer surface portion, along the posterior aspect of a corresponding one of the condylar surface and the articular surface so as to maintain essential congruency between the profile contour configurations and thereby enable an increased area of contact and decreased stress between the condylar surface and the articular surface while militating against distraction of the knee prosthesis during articulation through deep flexion.

2. The improvement of claim 1 wherein the inner surface portion is flared outwardly, in a direction away from the outer surface portion, along the posterior aspect of the condylar surface.

3. The improvement of claim 2 wherein articulation of the knee prosthesis is enabled up to about 150° of flexion.

4. The improvement of claim 2 wherein rotation about the longitudinal axis of rotation is enabled up to about 12° to 15° of rotation, during flexion up to about 150° of flexion.

5. The improvement of claim 2 wherein the flared surface portion extends along the posterior aspect of the condylar surface from a location corresponding to about 90° of flexion to a location corresponding to about 150° of flexion.

6. The improvement of claim 5 wherein the predetermined curvature of the prescribed track is generally arcuate.

7. The improvement of claim 1 wherein a least one of the inner surface portion and the outer surface portion is flared along the anterior aspect of at least a corresponding one of the condylar surface and the articular surface so as to maintain essential congruency between the profile contour configurations and thereby enable an increased area of contact and decreased stress between the condylar surface and the articular surface while militating against distraction of the knee prosthesis during articulation through hyperextension.

8. The improvement of claim 7 wherein the outer surface portion is flared inwardly, in a direction away from the inner surface portion, along the anterior aspect of the articular surface.

9. The improvement of claim 8 wherein articulation of the knee prosthesis is enabled up to about 12° of hyperextension.

10. The improvement of claim 8 wherein rotation about the longitudinal axis of rotation is enabled up to about 3° to 6° of rotation, during hyperextension up to about 12° of hyperextension.

11. The improvement of claim 10 wherein the flared surface portion extending along the anterior aspect of the articular surface extends from a location corresponding to about 0° of flexion to a location corresponding to about 12° of hyperextension.

12. The improvement of claim 11 wherein the predetermined curvature of the prescribed track is generally arcuate.

13. The improvement of claim 1 wherein the profile contour configuration of the inner surface portion includes a concave contour along the posterior aspect of the condylar surface and the profile contour configuration of the outer surface portion includes a convex contour along the posterior aspect of the articular surface for engaging the concave contour during articulation of the knee prosthesis through deep flexion.

14. The improvement of claim 13 wherein the profile contour configuration of the inner surface portion includes a concave contour along the anterior aspect of the condylar surface and the profile contour configuration of the outer surface portion includes a convex contour along the anterior aspect of the articular surface for engaging the concave contour during articulation of the knee prosthesis through hyperextension.

15. The improvement of claim 1 wherein the condylar surface follows prescribed radii of curvature about the transverse axis of rotation, a prescribed radius of curvature of posterior portions of the condylar surface engaged by the articular surface during articulation of the knee prosthesis beyond about 110° of flexion being smaller than a prescribed radius of curvature of portions of the condylar surface engaged by the articular surface during articulation up to about 110° of flexion.

16. The improvement of claim 15 wherein a prescribed radius of curvature of portions of the condylar surface engaged by the articular surface during articulation of the knee prosthesis between about 10° and 110° of flexion is smaller than a prescribed radius of curvature of portions of the condylar surface engaged by the articular surface during articulation up to about 10° of flexion.

17. In a knee prosthesis for implantation to replace a natural knee joint, the knee prosthesis having a femoral component including at least one condylar element with a condylar surface having a transverse axis of rotation, and a tibial component including at least one articular surface configured for engagement with the condylar surface of the femoral component during articulation of the knee prosthesis about the transverse axis of rotation, with the condylar surface and the articular surface engaged along corresponding posterior aspects during flexion, and along corresponding anterior aspects during hyperextension, the condylar surface and the articular surface being configured for enabling engagement between the condylar surface and the articular surface along a prescribed track having a predetermined curvature which enables relative rotational movement between the femoral component and the tibial component about a longitudinal axis of rotation during articulation about the transverse axis of rotation, the condylar surface and the articular surface including profile contour configurations in generally medial-lateral longitudinal planes, the condylar surface having an inner surface portion confronting the longitudinal axis of rotation, and the articular surface having an outer surface portion for engagement with the inner surface portion during articulation:

an improvement wherein at least one of the inner surface portion and the outer surface portion is flared in a direction away from a corresponding other of the inner surface portion and the outer surface portion, along the anterior aspect of at least a corresponding one of the condylar surface and the articular surface so as to maintain essential congruency between the profile contour configurations and thereby enable an increased area of contact and decreased stress between the condylar surface and the articular surface while militating against distraction of the knee prosthesis during articulation through hyperextension.

18. The improvement of claim 17 wherein the outer surface portion is flared inwardly, in a direction away from the inner surface portion, along the anterior aspect of the articular surface.

19. The improvement of claim 18 wherein articulation of the knee prosthesis is enabled up to about 12° of hyperextension.

20. The improvement of claim 18 wherein rotation about the longitudinal axis of rotation is enabled up to about 3° to 6° of rotation, during hyperextension up to about 12° of hyperextension.

21. The improvement of claim 20 wherein the flared surface portion extending along the anterior aspect of the articular surface extends from a location corresponding to about 0° of flexion to a location corresponding to about 12° of hyperextension.

22. The improvement of claim 21 wherein the predetermined curvature of the prescribed track is generally arcuate.

23. In a knee prosthesis for implantation to replace a natural kneejoint, the knee prosthesis having a femoral component including a lateral condylar element and a medial condylar element, each condylar element including a condylar surface having a transverse axis of rotation, and a tibial component including a lateral articular surface and a medial articular surface, each articular surface being configured for engagement with a corresponding condylar surface of the femoral component during articulation of the knee prosthesis about the transverse axis of rotation, with the condylar surfaces and the articular surfaces engaged along corresponding posterior aspects during deep flexion, and along corresponding anterior aspects during hyperextension, each condylar surface and each articular surface being configured for enabling engagement between the condylar surfaces and corresponding articular surfaces along respective prescribed tracks each having a predetermined curvature which enable relative rotational movement between the femoral component and the tibial component about a longitudinal axis of rotation during articulation about the transverse axis of rotation, the condylar surfaces and the articular surfaces including profile contour configurations in generally medial-lateral longitudinal planes, the condylar surfaces each having an inner surface portion confronting the longitudinal axis of rotation and the articular surfaces each having an outer surface portion for engagement with a corresponding inner surface portion during articulation:

an improvement wherein at least one of the inner surface portions and the outer surface portions is flared in a direction away from a corresponding other of the inner surface portions and the outer surface portions, along the posterior aspect of at least a corresponding one of the condylar surfaces and articular surfaces so as to maintain essential congruency between the profile contour configurations and thereby enable an increased area of contact and decreased stress between the condylar surfaces and the articular surfaces while militating against distraction of the knee prosthesis during articulation through deep flexion.

24. The improvement of claim 23 wherein each inner surface portion is flared outwardly, in a direction away from a corresponding outer surface portion, along the posterior aspect of the condylar surface.

25. The improvement of claim 24 wherein articulation of the knee prosthesis is enabled up to about 150° of flexion.

26. The improvement of claim 24 wherein rotation about the longitudinal axis of rotation is enabled up to about 12° to 15° of rotation, during flexure up to about 150° of flexion.

27. The improvement of claim 24 wherein the flared surface portions extend along the posterior aspects of the condylar surfaces from locations corresponding to about 90° of flexion to locations corresponding to about 150° of flexion.

28. The improvement of claim 27 wherein the predetermined curvature of each prescribed track is generally arcuate.

29. The improvement of claim 23 wherein at least one of the inner surface portions and the outer surface portions is flared in a direction away from the other of the inner surface portions and the outer surface portions along the anterior aspect of at least a corresponding one of the corresponding condylar surfaces and the articular surfaces so as to maintain essential congruency between the profile contour configurations and thereby enable an increased area of contact and decreased stress between the condylar surfaces and the articular surfaces while militating against distraction of the knee prosthesis during articulation through hyperextension.

30. The improvement of claim 29 wherein each outer surface portion is flared inwardly, in a direction away from a corresponding inner surface portion, along anterior aspects of the articular surfaces.

31. The improvement of claim 30 wherein articulation of the knee prosthesis is enabled up to about 12° of hyperextension.

32. The improvement of claim 30 wherein rotation about the longitudinal axis of rotation is enabled up to about 3° to 6° of rotation, during hyperextension up to about 12° of hyperextension.

33. The improvement of claim 30 wherein the flared surface portions extending along the anterior aspects of the articular surfaces extend from locations corresponding to about 0° of flexion to locations corresponding to about 12° of hyperextension.

34. The improvement of claim 33 wherein the predetermined curvature of each prescribed track is generally arcuate.

35. The improvement of claim 23 wherein the profile contour configuration of each inner surface portion includes a concave contour along the posterior aspect of the corresponding condylar surface and the profile contour configuration of each outer surface portion includes a convex contour along the posterior aspect of the corresponding articular surface for engaging a respective concave contour during articulation of the knee prosthesis through deep flexion.

36. The improvement of claim 35 wherein the profile contour configuration of each inner surface portion includes a concave contour along the anterior aspect of the corresponding condylar surface and the profile contour configuration of each outer surface portion includes a convex contour along the anterior aspect of the corresponding articular surface for engaging a respective concave contour during articulation of the knee prosthesis through hyperextension.

37. The improvement of claim 23 wherein each condylar surface follows prescribed radii of curvature about the transverse axis of rotation, a prescribed radius of curvature of posterior portions of each condylar surface engaged by a corresponding articular surface during articulation of the knee prosthesis beyond about 110° of flexion being smaller than a prescribed radius of curvature of portions of each condylar surface engaged by a corresponding articular surface during articulation up to about 110° of flexion.

38. The improvement of claim 37 wherein a prescribed radius of curvature of portions of each condylar surface engaged by a corresponding articular surface during articulation of the knee prosthesis between about 10° and 110° of flexion is smaller than a prescribed radius of curvature of portions of each condylar surface engaged by a corresponding articular surface during articulation up to about 10° of flexion.

39. In a knee prosthesis for implantation to replace a natural knee joint, the knee prosthesis having a femoral component including a lateral condylar element and a medial condylar element, each condylar element including a condylar surface having a transverse axis of rotation, and a tibial component including a lateral articular surface and a medial articular surface, each articular surface being configured for engagement with a corresponding condylar surface of the femoral component during articulation of the knee prosthesis about the transverse axis of rotation, with the condylar surfaces and the articular surfaces engaged along corresponding posterior aspects during flexion, and along corresponding anterior aspects during hyperextension, each condylar surface and each articular surface being configured for enabling engagement between the condylar surfaces and corresponding articular surfaces along respective prescribed tracks each having a predetermined curvature which enables relative rotational movement between the femoral component and the tibial component about a longitudinal axis of rotation during articulation about the transverse axis of rotation, the condylar surfaces and the articular surfaces including profile contour configurations in generally medial-lateral longitudinal planes, the condylar surfaces each having an inner surface portion confronting the longitudinal axis of rotation and the articular surfaces each having an outer surface portion for engagement with a corresponding inner surface portion during articulation:

an improvement wherein at least one of the inner surface portions and the outer surface portions is flared, in a direction away from a corresponding other of the inner surface portions and the outer surface portions, along the anterior aspect of at least a corresponding one of the condylar surfaces and articular surfaces so as to maintain essential congruency between the profile contour configurations and thereby enable an increased area of contact and decreased stress between the condylar surfaces and the articular surfaces while militating against distraction of the knee prosthesis during articulation through hyperextension.

40. The improvement of claim 39 wherein each outer surface portion is flared inwardly, in a direction away from a corresponding inner surface portion along the anterior aspects of the articular surfaces.

41. The improvement of claim 40 wherein articulation of the knee prosthesis is enabled up to about 12° of hyperextension.

42. The improvement of claim 40 wherein rotation about the longitudinal axis of rotation is enabled up to about 3° to 6° of rotation, during hyperextension up to about 12° of hyperextension.

43. The improvement of claim 42 wherein each flared surface portion extending along the anterior aspect of the articular surfaces extends from a location corresponding to about 0° of flexion to a location corresponding to about 12° of hyperextension.

44. The improvement of claim 43 wherein the predetermined curvature of each prescribed track is generally arcuate.

* * * * *